United States Patent
Go et al.

(10) Patent No.: US 9,671,353 B2
(45) Date of Patent: Jun. 6, 2017

(54) APPARATUS AND SYSTEM FOR PEST DETECTION, AND METHOD FOR DETECTING PEST DAMAGE

(71) Applicants: GANGNEUNG-WONJU NATIONAL UNIVERSITY INDUSTRY ACADEMY COOPERATION GROUP, Gangwon-do (KR); Hyeong Sun Go, Gangwon-do (KR); SEOLBONG CO., LTD., Gangwon-do (KR)

(72) Inventors: Hyeong Sun Go, Gangwon-do (KR); Byoung Hoon Lee, Gangwon-do (KR); Byung Hak Choe, Gangwon-do (KR); Hyo Tae Jeong, Gangwon-do (KR); Jong Heon Shim, Gangwon-do (KR)

(73) Assignees: Gangneung-Wonju National University Industry Academy Cooperation Group, Gangneung-si, Gangwon-do (KR); Seolbong Co., Ltd., Gangneung-si, Gangwon-do (KR); Hyeong Sun Go, Chuncheon-si, Gangwon-do (KR)

( * ) Notice: Subject to any disclaimer, the term of this patent is extended or adjusted under 35 U.S.C. 154(b) by 0 days.

(21) Appl. No.: 14/774,159

(22) PCT Filed: Mar. 5, 2014

(86) PCT No.: PCT/KR2014/001787
§ 371 (c)(1),
(2) Date: Sep. 10, 2015

(87) PCT Pub. No.: WO2014/142462
PCT Pub. Date: Sep. 18, 2014

(65) Prior Publication Data
US 2016/0025652 A1    Jan. 28, 2016

(30) Foreign Application Priority Data

Mar. 11, 2013  (KR) .................. 10-2013-0025526

(51) Int. Cl.
*G01N 21/00* (2006.01)
*G01N 21/954* (2006.01)
(Continued)

(52) U.S. Cl.
CPC ........... *G01N 21/954* (2013.01); *A01M 1/026* (2013.01); *A01M 1/24* (2013.01); *G01N 33/46* (2013.01);
(Continued)

(58) Field of Classification Search
CPC ........... A01M 1/026; A01M 1/24; E04B 1/72; G01N 2021/9544; G01N 21/954; G01N 33/46
(Continued)

(56) References Cited

U.S. PATENT DOCUMENTS 5,877,422 A    3/1999    Otomo

FOREIGN PATENT DOCUMENTS

JP    2004-008161 A    1/2004
JP    3115318 U9    9/2005
(Continued)

*Primary Examiner* — Tri T Ton
(74) *Attorney, Agent, or Firm* — Rabin & Berdo, P.C.

(57) ABSTRACT

Provided are apparatus and system for pest detection and a method for detecting pest damage to prevent pest damage in wooden building structures. The apparatus according to one aspect of the present invention comprises: a post-shaped main body extending in a set direction and formed therealong, and comprising a plurality of holes distanced from each other with a wall therebetween, the wall comprising timber which can be despoiled by pest; and a sensor unit allowing attachment and detachment to and from the upper (Continued)

end of the main body. Here, the sensor unit may comprise: a light-emitting unit comprising at least one light-emitting body for irradiating the interior of at least one hole among the plurality of holes; a sensing unit for sensing the light, emitted from the light-emitting unit, in the interior of at least one hole from among the plurality of holes; and a detection unit for outputting a light signal received from the sensing unit as an electrical signal.

11 Claims, 5 Drawing Sheets

(51) Int. Cl.
    *A01M 1/24*         (2006.01)
    *A01M 1/02*         (2006.01)
    *G01N 33/46*        (2006.01)
    *E04B 1/72*          (2006.01)

(52) U.S. Cl.
    CPC ........ *E04B 1/72* (2013.01); *G01N 2021/9544* (2013.01)

(58) Field of Classification Search
    USPC ...................... 356/238.3–239.8, 240.1–241.6
    See application file for complete search history.

(56) References Cited

FOREIGN PATENT DOCUMENTS

| | | |
|---|---|---|
| KR | 10-1997-0049923 A | 7/1997 |
| KR | 10-2009-0043788 A | 5/2009 |

APPARATUS AND SYSTEM FOR PEST DETECTION, AND METHOD FOR DETECTING PEST DAMAGE

TECHNICAL FIELD

The present invention is related to an apparatus and system for pest detection and a method for detecting pest damage. In particular, the present invention is related to an apparatus and system for pest detection and a method for detecting pest damage so as to minimize pest damage in wooden building structures.

BACKGROUND ART

Generally, a technology of detecting pests is used for prevention of damage on wooden buildings. In particular, for wooden cultural properties, the loss of cultural values cannot be recovered after damage occurs. In addition, repair is not easy and a significant cost is required to repair it.

One of Most harmful pests to wooden building structures is a termite. The termite is harmful to dried wood and damp wood. The termite prefers conifers to broadleaved trees, sapwoods to heartwoods, and early woods to late woods. In particular, since the termite likes pine trees, the termite is a major harmful pest to traditional wooden buildings made of pine trees.

Since the termite does not light, the termite is harmful to the inside of woods. Accordingly, it is difficult to realize the progress of damage in wooden buildings by eyesight. When the damage is realized, the degree of the damage is already significant. Therefore, when a damage occurs in a building structure, the detection and control of termites is difficult. Various apparatuses and methods are used for prevention of damage on wooden buildings by termites and other pest For example, there is a conventional method for preventing damage on a wooden building in which baits are disposed on a ground near a building structure and the decrease of the baits is directly monitored.

In this case, the monitor of the decrease of the baits is performed by taking the baits form the ground, and thus the detection of damage may be late and proper countermeasure could not be provided on time.

DETAILED DESCRIPTION OF THE INVENTION

Technical Problem

The present invention has an objective to solve the above described problem and other problems. The present invention provides a pest detecting apparatus and system and a method for detecting damage with which pest damage can be detected in an early stage and the degree of the damage is immediately provided. However, this objective is only exemplary, and thus the scope of the present invention is not limited thereto.

Technical Solution

According to one aspect of the present invention, a pest detecting apparatus includes: a main body having a post-shape and extending in a predetermined direction, wherein the main body comprises a plurality of holes distanced from each other with a wall made of wood can be despoiled by pest therebetween; and a sensor unit attachable to and detachable from an upper end of the main body. Herein, the sensor unit comprises: a light-emitting unit comprising at least one light-emitting body for irradiating the interior of at least one hole among the plurality of the holes; a sensing unit for sensing the light emitted from the light-emitting unit disposed in the at least one hole among the plurality of the holes; and a detection unit for outputting a light signal received from the sensing unit as an electrical signal.

The light-emitting unit may include a plurality of light-emitting bodies respectively disposed in the plurality of the holes. The sensing unit may make a pair with at least one of the plurality of the light-emitting bodies to respectively dispose in each of the plurality of the holes.

The pest detecting apparatus further includes a wireless communication apparatus for receiving an electrical signal outputted from the detecting unit and wirelessly transmitting the electrical signal to an outer electronic apparatus.

According to one aspect of the present invention, a pest detecting system includes: at least one pest detecting apparatus described above; a wireless communication apparatus attached to the pest detecting apparatus for receiving a signal outputted from the detecting unit of the pest detecting apparatus and wirelessly transmitting the electrical signal to an outer electronic apparatus; and a processing unit for receiving and processing information transmitted from the wireless communication apparatus to output an output signal corresponding to the information received.

According to one aspect of the present invention, a method of detecting pest damages includes: a first step for inserting a main body into a ground and maintaining for a predetermined period, wherein the main body is made of wood has a post-shape and extends in a predetermined direction, wherein the main body comprises a plurality of holes extending in the predetermined direction and distanced from each other with a wall made of wood can be despoiled by pest therebetween, wherein the main body is covered by a cover to close upper portions of the holes; a second step for opening the cover, inserting a light-emitting unit in a first hole of the plurality of the holes, and inserting a sensing unit sensing light emitted from the light-emitting unit in a second hole; and a third step for emitting light from the light-emitting unit inserted into the first hole and sensing the light by the sensing unit inserted into the second hole to detect a presence of an aperture of wall between the first hole and the second hole caused by pest.

The second step may be for inserting a light-emitting unit and a sensing unit into each of the plurality of the holes. The third step may be for emitting light from the light-emitting unit inserted into the first hole and sensing the light by the sensing units inserted into the holes except the first hole to detect a presence of an aperture of wall between the first hole and each of other holes caused by pest.

The method of detecting pest damages may further includes: a fourth step, after performing the third step, for emitting light from a light-emitting unit inserted into at least one hole except the first hole and sensing the light by the sensing units inserted into the holes except the hole into which the light-emitting unit emitting light is inserted.

Advantageous Effects

According to the embodiments of the present invention, pest damage on wooden building is immediately detected and a signal representing the damage is obtained in an early stage, thereby minimizing pest damage on the wooden building. The advantage of the present invention is not limited thereto, but other advantages not mentioned can be understood by a skilled person in the field of the present invention for the following description.

BEST MODE

Figure 1:
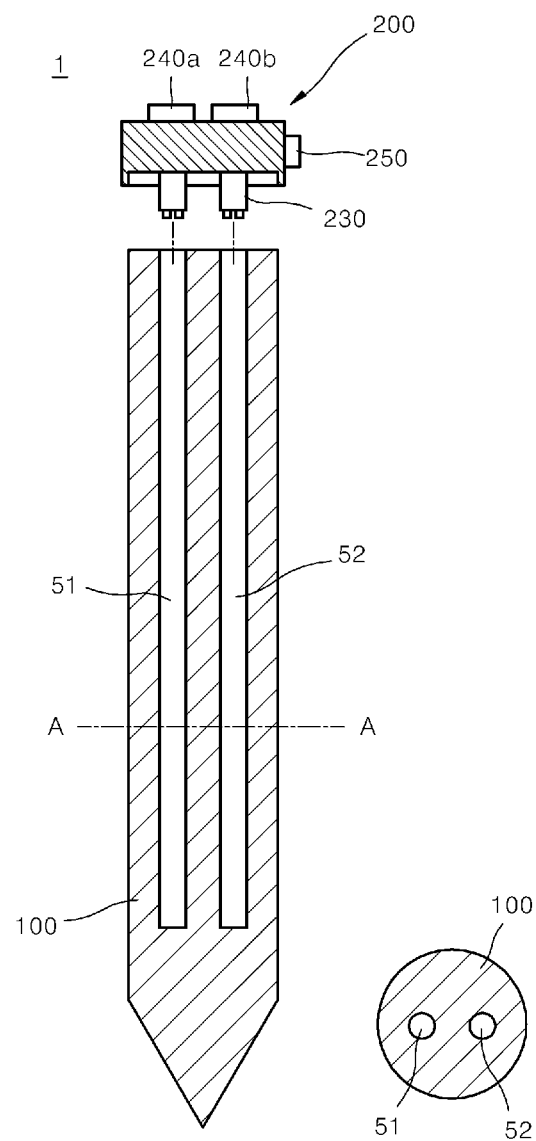
FIG. 1 and FIG. 2 are schematic diagrams showing a cross-section of a pest detecting apparatus, according to an embodiment of the present invention.

Reference will now be made in detail to exemplary embodiments, examples of which are illustrated in the accompanying drawings. However, exemplary embodiments are not limited to the embodiments illustrated hereinafter, and the embodiments herein are rather introduced to provide easy and complete understanding of the scope and spirit of exemplary embodiments. In the drawings, the sizes of components are exaggerated or reduced for easy description.

Figure 2:
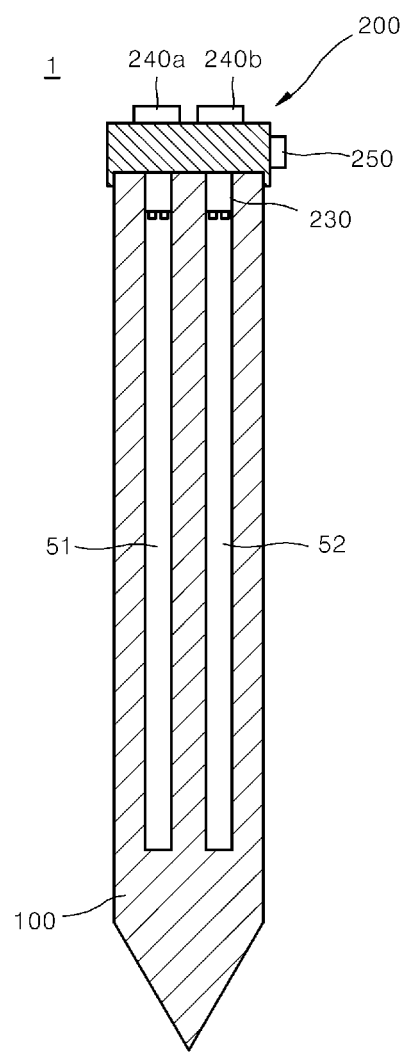

In FIG. 1 and FIG. 2 show cross-section diagrams of a pest detecting apparatus 1 according to an embodiment of the present invention. Referring to FIG. 1 and FIG. 2, the pest detecting apparatus 1 includes a main body 100 and a sensor unit 200 attachable to and detachable from the main body 100.

The main body 100 is made of wood and has a post shape extending a predetermined direction with a sharp edge. Due to the post shape, the main body 100 can be easily inserted into a ground near a wooden building structure. The main body 100 may be made of wood incentive to pests. For example, the main body 100 may be made of a pine tree, a Douglas fir, a Japanese larch, a hemlock spruce, a Korean spruce, a willow, or the like which is vulnerable to pests such as termites.

A plurality of holes 51, 52 may be formed along the extending direction of the main body 100 inside of the main body 100. The plurality of holes 51 and 52 are distanced from each other with a wall therebetween. The wall may include of wood despoiled by pests. The wall disposed between the hole 51 and the hole 52 may block travel of light therebetween. However, when a through-hole is formed on the wall by pest damage, light can travel between the hole 51 and the hole 52 through the through-hole. In the lower right of FIG. 1, a cross-section of the main body 100 cut through the line A-A is shown. In FIG. 1, the holes 51, 52 have circular cross-sections, but the present invention is not limited thereto. The holes 51, 52 may have various cross-section shapes.

The sensor unit 200 has a structure attachable to an upper end of the main body 100 so as to cover upper openings of the holes 51, 52 and isolate the holes 51, 52 from the outside. The sensor unit 200 is not fixed at the upper end of the main body 100. The sensor unit 200 has a structure attachable and detachable to the main body 100, if necessary. FIG. 1 shows how to combine the sensor unit 200 and the main body 100. FIG. 2 shows that the sensor unit 200 is combined with the main body 100.

Figure 3:
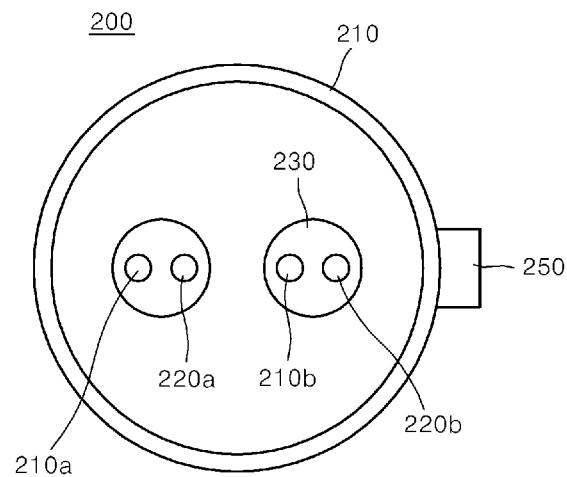
FIG. 3 and FIG. 4 are a cross-section diagram and a perspective diagram of a sensor unit, respectively, according to an embodiment of the present invention.
Figure 4:
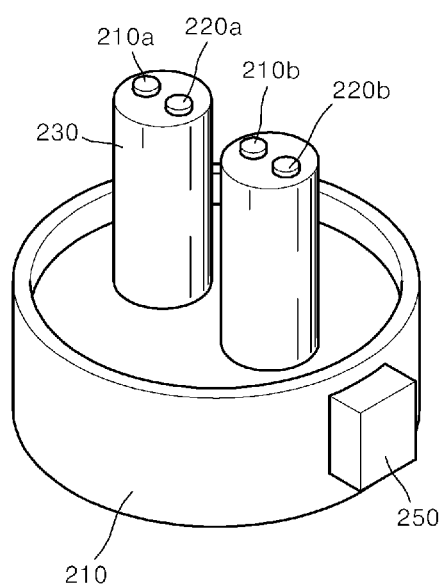

FIG. 3 and FIG. 4 are a cross-section diagram and a perspective diagram of a sensor unit 200, respectively, according to an embodiment of the present invention. Referring to FIG. 1 through FIG. 4, the sensor unit 200 includes light-emitting units 210a, 210b emitting light, sensing units 220a, 220b sensing the light emitted from the light-emitting units 210a, 210b, and detecting units 240a, 240b outputting an electric signal from the light signal received from the sensing units 220a, 220b.

The sensor unit 200 has a shape attachable to the upper end of the main body. For example, the sensor unit 200 has a body having lower portion whose area is approximately same as the area of the upper end of the main body 100. However, the present invention is not limited thereto. The sensor unit 200 may have any structure with which the sensor unit 200 is attached to the upper end of the main body 100 and closes the upper openings of the holes 51, 52 formed in the main body 100.

The light-emitting units 210a, 210b are light source generating light. The light-emitting units 210a, 210b are disposed at a surface of the sensor unit 200. The light-emitting units 210a, 210b include at least one light-emitting body irradiating the interior of at least one hole among the plurality of the holes 51, 52. The light-emitting body may have a heat lamp, LED, or the like. The light-emitting body may have various light sources within the scope of the present invention.

The sensing units 220a, 220b sense the light emitted from the light-emitting unit 200 to detect as electrical signals. The sensing units 220a, 220b may be referred as sensors.

The light-emitting units 210a, 210b and the sensing units 220a, 220b have sizes and arrangements so as to insert into the inner spaces of the holes 51, 52, respectively. For example, when the sensor unit 200 is combined with the main body 100, the light-emitting units 210a, 210b and the sensing units 220a, 220b are distanced from a contact surface of the sensor unit 200 contacting the main body 100 so as to insert into the inner spaces of the holes 51, 52, respectively. In this case, as shown in FIG. 4, the sensor unit 200 may have a plurality of extending structures 230 extending from the contact surface of the sensor unit 200 contacting the main body 100. One of the light-emitting units 210a, 210b and one of the sensing units 220a, 220b make a pair to dispose together at the end of the extending structure 230.

When the sensor unit 200 is combined with the main body 100, the extending structures 230a, 230b are inserted into the holes 51, 52, respectively. The each pair of the light-emitting units 210a, 210b and the sensing units 220a, 220b are disposed inside of the holes 51, 52, respectively. The sensor unit 200 closes the upper openings of the holes 51, 52 so as to prevent the interiors of the holes 51, 52 from irradiating.

When the sensor unit 200 is detached from the main body 100, the light-emitting units 210a, 210b and the sensing units 220a, 220b are removed, thereby exposing the inner spaces of the holes 51, 52.

The detecting units 240a, 240b is electrically connected to the sensing units 210a, 210b, respectively, thereby generating electrical signals by processed the light sensed by the sensing units 210a, 210b. The detecting units 240a, 240b have various output apparatuses with which a user can confirm the generation of the electrical signals.

In the above embodiment, the number of the holes formed in the main body 100 is two, but the present invention is not limited thereto. The number of the holes may be more than two. In addition, the number of the pair of the light-emitting unit and the sensing unit corresponds to the number of the holes. As the number of the holes increases, the distance between the holes decreases to increase the density of the holes formed in the main body 100, thereby providing accurate detection of the pest damage. The number of the holes can be determined according to the necessity of protecting values of the building structures.

As a modified embodiment, the light-emitting unit and the sensing unit in the sensor unit may not make a pair and be disposed separately inside of different holes. For example, as a modification of the pest detecting apparatus 1 in FIG. 1, a light-emitting unit is disposed to insert into the hole 51 and a sensing unit is dispose to insert into the hole 52.

The pest detecting apparatus 1 may further include a wireless communication apparatus 250 for receiving signals outputted from the detecting units 240a, 240b of the pest detecting apparatus 1 and wirelessly outputting the signals to a outer electronic apparatus. By using the wireless communication apparatus 250, a pest detection system with wireless communication can be realized, as described later.

Hereinafter, method of detecting pest damage using the pest detecting apparatus 1 will be described with reference with FIG. 1 and FIG. 2, according to an embodiment of the present invention.

At least one main body 100 is inserted into a ground adjacent to a old wooden building, for example a cultural property, and maintained for a predetermined period. Herein, the main body 100 is covered by a cover not to expose the holes 51, 52, thereby preventing the interior of the holes 51, 52 from being damaged by rain falls, dusts, or other environment factors.

After the predetermined period, the cover is removed and the sensor unit 200 is combined with the upper end of the main body 100, as shown in FIG. 2. During the combination, the light-emitting unit 210a and the sensing unit 220a are inserted into the hole 51, and the light-emitting unit 210b and the sensing unit 220b are inserted into the hole 52.

Next, when the light-emitting unit 210a in the hole 51 begins to emit light, the sensing unit 220b in the hole 52 may or may not senses the light emitted from the light-emitting unit 210a. When the hole 51 and the hole 52 are isolated each other by the wall, for example, when the main body 100 is inserted into the ground, the light emitted from the light-emitting unit 210a disposed in the hole 51 is not sensed by the sensing unit 220b disposed in the hole 52. In this case, the pest damage may not occur or be insignificant.

Figure 5:
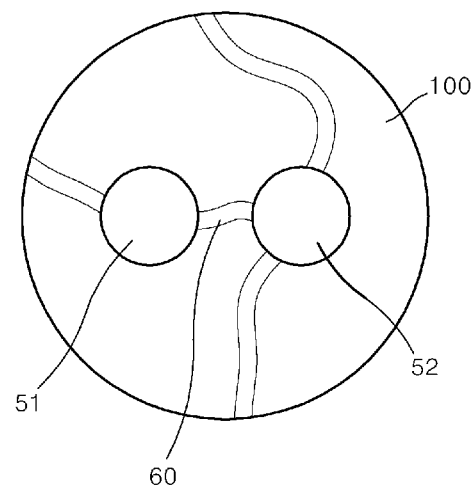
FIG. 5 and FIG. 6 are diagrams showing cross-sections of the pest detecting apparatus damaged by pests, according to another embodiment of the present invention.

However, when the main body 100 made of wood is damaged by pests, such as termites, the wall between the hole 51 and the hole 52 is damaged to form an aperture 60, as shown in FIG. 5. When the aperture 60 is formed, a light pathway between the hole 51 and the hole 52 is formed, and then the light emitted from the light-emitting unit 210a disposed in the hole 51 moves through the aperture 60 and may be sensed by the sensing unit 220b disposed in the hole 52.

The light sensed by the sensing unit 220b is transformed to electrical signals and the electrical signals are outputted by an output apparatus in the detecting unit 240b. For example, the intensity of the light may be indicated by a graph on a monitor, by a alarm sound, by turning on a lamp, or by blinking a lamp.

A user, for example a cultural property's custodian, reads the output result through the output apparatus and then predicts a degree of the pest damage on a cultural property near the pest detecting apparatus 1 through the pest damage of the pest detecting apparatus 1. Therefore, the user can prepare a countermeasure.

Accordingly, the method of detecting pest damage performed by emitting and sensing light can be applied to another pest detecting apparatus in which the light-emitting unit and the sensing unit does not make a pair and are disposed separately inside of different holes.

As another embodiment of the method of detecting pest damage, a plurality of light-emitting units sequentially emit light and then a plurality of sensing units sequentially sense the light. For example, the light-emitting unit 210b does not emit light, the light-emitting unit 210a emit light, and the sensing unit 220a and the sensing unit 220b sense the light. After that, the light-emitting unit 210a does not emit light, the light-emitting unit 210b emits light, the sensing unit 220a and the sensing unit 220b sense the light.

When the wall between the hole 51 and the hole 52 is not damaged, the light emitted from the light-emitting unit 210a disposed in the hole 51 is sensed only by the sensing unit 220a, and the light emitted from the light-emitting unit 210b disposed in the hole 52 is sensed only by the sensing unit 220b.

However, when the wall between the hole 51 and the hole 52 is damaged to form an aperture 60, as shown in FIG. 5, a light pathway between the hole 51 and the hole 52 is formed. Accordingly, the light emitted from the light-emitting unit 210a is sensed by both the sensing unit 220a and the sensing unit 220b and the light emitted from the light-emitting unit 210b is sensed by both the sensing unit 220a and the sensing unit 220b.

Accordingly, the plurality of light-emitting units sequentially emit lights and a sensing unit disposed in a hole in which the light-emitting unit emitting light and other sensing unit disposed in a different hole sense the light together, thereby detecting the aperture of the wall so as to increase the detection accuracy of the pest damage.

Figure 6:
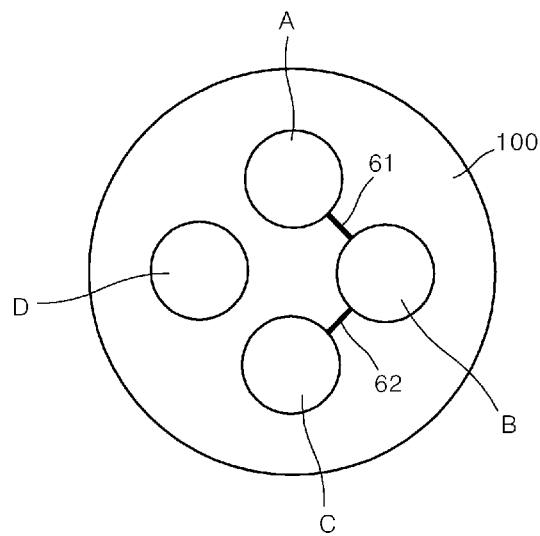

As another embodiment of the present invention, a sensing manner of the sensing unit according to damage pathway of the main body with reference of FIG. 6. In FIG. 6, the main body 100 has four holes A, B, C, D. An aperture 61 is formed between the hole A and the hole B. An aperture 62 is formed between the hole B and the hole D.

Table 1 shows the results that the sensing units inserted the holes A, B, C, D are sensed the lights sequentially emitted from light-emitting units inserted in the holes A, B, C, D. "◯" indicates when the sensing unit senses the light emitted from the light-emitting unit. "X" indicates when the sensing unit does not sense the light emitted from the light-emitting unit. The sensing unit A and the light-emitting unit A indicate the sensing unit and the light-emitting unit inserted in to the hole A. The sensing unit B and the light-emitting unit B indicate the sensing unit and the light-emitting unit inserted in to the hole B. The sensing unit C and the light-emitting unit C indicate the sensing unit and the light-emitting unit inserted in to the hole C. The sensing unit D and the light-emitting unit D indicate the sensing unit and the light-emitting unit inserted in to the hole D.

TABLE 1

|  | sensing unit A | sensing unit B | sensing unit C | sensing unit D |
|---|---|---|---|---|
| light-emitting unit A | ◯ | ◯ | X | ◯ |
| light-emitting unit B | ◯ | ◯ | X | ◯ |
| light-emitting unit C | X | X | ◯ | X |

TABLE 1-continued

|  | sensing unit A | sensing unit B | sensing unit C | sensing unit D |
|---|---|---|---|---|
| light-emitting unit D | O | O | X | O |

Figure 7:
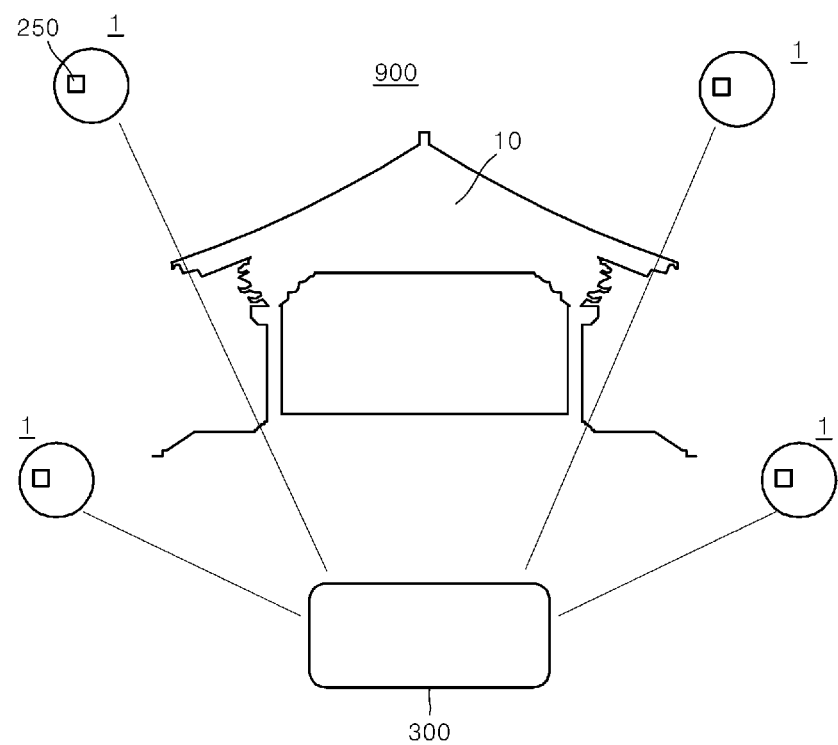
FIG. 7 is a schematic diagram showing a pest detection system, according to another embodiment of the present invention.

For example, referring to FIG. 7 and Table 1, when a light-emitting unit A disposed in the hole A emit light, the sensing unit A disposed in the hole A sense the light. In addition, the sensing unit B disposed in the hole B and the sensing unit D disposed in the hole D also sense the light because the light transmits through the aperture 61 and the aperture 62. However, the hole C is not connected to the hole A, the sensing unit C disposed in the hole C cannot sense the light emitted from the light-emitting unit disposed in the hole A.

Next, the light-emitting units disposed in the hole B, the hole C, and the hole D sequentially emit light and the sensing units disposed in the hole A, the hole B, the hole C, and the hole D sense the light. Table 1 shows the result of sensing the light by the sensing units. By the results of output signals in Table 1, a damaged pathway among the holes A, B, D can be accurately detected.

There is a system having the pest detecting apparatus with wireless communication, according to an embodiment of the present invention. In FIG. 7, a pest detection system 900 with wireless communication is schematically shown. Referring to FIG. 7, the pest detection system include the pest detecting apparatus 1 of the present invention ಇ pest detecting apparatus 1 and a component processing the signal detected by the pest detecting apparatus 1.

The pest detection system 900 includes a wireless communication apparatus 250 and a processing unit 300. The wireless communication apparatus 250 is attached to the pest detecting apparatus 1, receives the signal outputted from the detecting unit in the pest detecting apparatus, and output the signals with wireless communication to an outer electronic apparatus. The processing unit 300 receives and processes the signals from the wireless communication apparatus 250 and then outputs an output signal corresponding to the received signals.

The wireless communication apparatus 250 transmits the electrical signal from the detecting unit to processing unit 300. The wireless communication apparatus 250 can transmit signals to the processing unit 300 in a long distance. The wireless communication apparatus 250 may be attached to the main body or distanced from the main body, if necessary. The wireless communication network used for the wireless communication apparatus 250 of the present invention may be a wireless communication network using one of AM, FM, PM, ASK, QSK, PSK, or the like.

The processing unit 300 receives and processes signals from the wireless communication apparatus 250 to output signals corresponding to the received signals. The processing unit 300 may include a signal receiving and transmitting unit (not shown), a control unit (not shown), and an output unit.

The signal receiving and transmitting unit receives an electrical signal from the wireless communication apparatus 250 and transmits it to the control unit.

The control unit receives and processes the information from the signal receiving and transmitting unit, and then output it to the output unit.

The output unit expresses the output signal processed in the control unit. The output unit may include visual means or auditory means. The auditory means includes an alarm sound, a calling sound, vibrating sound, or the like. The visual means includes a display like LCD showing the output results, a movable flag according to the output information, an alarm lamp, or the like. The visual means and auditory means may be used together. The use of the visual means and auditory means can be selected according to the position of a user or environmental factors.

The processing unit may be a personal communication apparatus transmitting information such as a smart phone, a tablet, a PC, or the like. In this case, a real time surveillance by a custodian is possible. For example, a custodian can performs the surveillance of the pest damage even when he is not near a cultural property, thereby immediately preparing a countermeasure against the pest damage.

When the pest detection system 900 is used, at least one pest detecting apparatus 1 disposed near a cultural property 10 periodically performs emitting light by the light-emitting unit and sensing the light by the sensing unit. When the pest detecting apparatus 1 senses a damage in the main body, for example creation of an aperture between the holes, the pest detecting apparatus 1 transmits the information of the damage to the control unit 300 through the wireless communication apparatus 250.

The processing unit receives and processing the information to output a results through the output unit for the custodian. For example, a warning sign is displayed on a display, a flag is simply raised, a warning lamp turns on, or a warning alarm generates. For example, a warning sign is displayed with information of the number of the pest detection unit detecting pest damage.

Accordingly, the custodian knows whether pest damage on the cultural property is occurring, and then can immediately prepare a countermeasure.

The foregoing is illustrative of exemplary embodiments and is not to be construed as limiting thereof. Although exemplary embodiments have been described, those of ordinary skill in the art will readily appreciate that many modifications are possible in the exemplary embodiments without materially departing from the novel teachings and advantages of the exemplary embodiments. Accordingly, all such modifications are intended to be included within the scope of the claims. Exemplary embodiments are defined by the following claims, with equivalents of the claims to be included therein.

What is claimed is:

1. A pest detecting apparatus, comprising:
   a main body having a post-shape and extending in a predetermined direction, wherein the main body comprises a plurality of holes extending in the predetermined direction and distanced from each other with a wall made of wood that can be despoiled by pest; and
   a sensor unit attachable to and detachable from an upper end of the main body,
   wherein the sensor unit comprises:
      at least one light-emitting body for emitting light into an interior of at least one hole among the plurality of the holes,
      at least one sensor for sensing the light emitted from the at least one light-emitting body in the at least one hole among the plurality of the holes, and
      a detector for outputting a light signal received from the sensing unit as an electrical signal.

2. The pest detecting apparatus of claim 1, wherein the at least one light-emitting body is respectively disposed in each of the plurality of the holes, wherein the at least one sensor makes a pair with the at least one light-emitting body and is respectively disposed in each of the plurality of the holes.

3. The pest detecting apparatus of claim 1, further comprising:
a wireless communication apparatus for receiving an electrical signal outputted from the detector and wirelessly transmitting the electrical signal to an outer electronic apparatus.

4. A pest detection system, comprising:
at least one pest detecting apparatus of claim 1;
a wireless communication apparatus attached to the pest detecting apparatus for receiving a signal outputted from the detector of the pest detecting apparatus and wirelessly transmitting the electrical signal to an outer electronic apparatus; and
a processing unit for receiving and processing information transmitted from the wireless communication apparatus to output an output signal corresponding to the information received.

5. A method of detecting pest damages, the method comprising:
a first step for inserting a main body into a ground and maintaining for a predetermined period, wherein the main body is made of wood and has a post-shape and extends in a predetermined direction, wherein the main body comprises a plurality of holes extending in the predetermined direction and distanced from each other with a wall made of wood that can be despoiled by pest, wherein the main body is covered by a cover to close upper portions of the holes;
a second step for opening the cover, inserting a first light-emitting body into a first hole of the plurality of the holes, and inserting a first sensor for sensing light emitted from the light-emitting body into a second hole; and
a third step for emitting the light from the first light-emitting body inserted into the first hole and sensing the light by the first sensor inserted into the second hole to detect a presence of aperture in the wall disposed between the first hole and the second hole caused by pest.

6. The method of claim 5, further including,
in the second step, inserting a second light-emitting body and a second sensor into each of the plurality of the holes, and
in the third step, emitting the light from the first light-emitting body inserted into the first hole and sensing the light by the second sensor inserted into the holes except the first hole to detect the presence of aperture in walls disposed between the first hole and each of other holes caused by pest.

7. The method of claim 6, further comprising:
a fourth step, after performing the third step, for emitting light from the second light-emitting body inserted into at least one hole except the first hole and sensing the light by sensors inserted into the holes except the hole into which the second light-emitting body is inserted.

8. A pest detection system, comprising:
at least one pest detecting apparatus of claim 2;
a wireless communication apparatus attached to the pest detecting apparatus for receiving a signal outputted from the detector of the pest detecting apparatus and wirelessly transmitting the electrical signal to an outer electronic apparatus; and
a processing unit for receiving and processing information transmitted from the wireless communication apparatus to output an output signal corresponding to the information received.

9. The pest detecting apparatus of claim 1, wherein the light-emitting body is a lamp or a light-emitting diode (LED).

10. The pest detecting apparatus of claim 1, wherein the sensor is a light sensor.

11. The pest detecting apparatus of claim 1, wherein the detector is a processor.

* * * * *